(12) United States Patent
Lawinger (10) Patent No.: US 11,274,425 B2
(45) Date of Patent: Mar. 15, 2022

(54) DIALYSATE DISPOSAL APPARATUS

(71) Applicant: Sloan Valve Company, Franklin Park, IL (US)

(72) Inventor: Mark Lawinger, Franklin Park, IL (US)

(73) Assignee: Sloan Valve Company, Franklin Park, IL (US)

( * ) Notice: Subject to any disclaimer, the term of this patent is extended or adjusted under 35 U.S.C. 154(b) by 0 days.

(21) Appl. No.: 16/421,084

(22) Filed: May 23, 2019

(65) Prior Publication Data

US 2019/0360184 A1 Nov. 28, 2019

Related U.S. Application Data

(60) Provisional application No. 62/675,290, filed on May 23, 2018.

(51) Int. Cl.
*E03C 1/182* (2006.01)
*A61M 1/14* (2006.01)

(52) U.S. Cl.
CPC .............. *E03C 1/182* (2013.01); *A61M 1/14* (2013.01)

(58) Field of Classification Search
CPC ... E03C 1/14; E03C 1/18; E03C 1/182; E03C 1/26; E03C 1/262; E03C 1/264; E03C 1/057; A61M 1/14; A61M 1/1609; A61M 1/1621; A61M 1/1654; A61M 1/28; E03D 5/105; E03D 5/10; F16L 37/28; F16L 37/38; F16L 37/40
See application file for complete search history.

(56) References Cited

U.S. PATENT DOCUMENTS

| 2,700,773 | A | | 2/1955 | Colendar | |
| 3,289,218 | A | * | 12/1966 | Mehilos | A47J 47/20 4/654 |
| 4,128,905 | A | * | 12/1978 | Mathes | A47K 1/08 4/654 |
| 4,205,710 | A | * | 6/1980 | Dunicz | E03C 1/26 4/679 |
| 5,004,459 | A | | 4/1991 | Peabody et al. | |
| 5,452,484 | A | * | 9/1995 | Hill | E03C 1/181 4/658 |
| 6,926,239 | B1 | * | 8/2005 | DiMaggio | A61M 1/1656 248/206.1 |

(Continued)

FOREIGN PATENT DOCUMENTS

| AU | 2005246923 A1 | | 7/2007 | |
| CA | 2199575 A1 | * | 9/1997 | .......... A61M 39/045 |
| WO | 2007019615 A1 | | 2/2007 | |

OTHER PUBLICATIONS

Aug. 27, 2019—(WO) International Search Report—App No. PCT/US19/33789.

(Continued)

*Primary Examiner* — Erin Deery
(74) *Attorney, Agent, or Firm* — Banner & Witcoff, Ltd.

(57) ABSTRACT

A dialysate disposal apparatus includes a water supply assembly configured to provide water through a plumbing fixture. A fitting is configured to connect to a drain of the plumbing fixture and includes an inlet configured to receive dialysate effluent from a dialysis device. A controller regulates an amount of water flow through the water supply assembly.

21 Claims, 4 Drawing Sheets

(56) References Cited

U.S. PATENT DOCUMENTS

| | | | |
|---|---|---|---|
| 2005/0161563 A1* | 7/2005 | Dimaggio | A61M 1/167 |
| | | | 248/167 |
| 2006/0026860 A1 | 2/2006 | Blann et al. | |
| 2006/0096016 A1* | 5/2006 | Krowl | A47K 13/24 |
| | | | 4/341 |
| 2014/0047631 A1 | 2/2014 | Seibt | |
| 2015/0299993 A1 | 10/2015 | Danhi | |
| 2018/0030711 A1 | 2/2018 | Quesada et al. | |
| 2019/0275217 A1* | 9/2019 | Suarez del Real Pena | |
| | | | A61M 1/0021 |

OTHER PUBLICATIONS

Sep. 5, 2019—(WO) International Search Report—App No. PCT/US2019/33793.
Sep. 1, 2021—(CN) Office Action—App 201980042986.X—Trans.
Dec. 1, 20214—(IN) First Examination Report—App 202047054291.

* cited by examiner

DIALYSATE DISPOSAL APPARATUS

CROSS-REFERENCE TO RELATED APPLICATION

This application is a non-provisional of, and claims priority to, U.S. Provisional Application No. 62/675,290, filed May 23, 2018, which prior application is incorporated by reference herein in its entirety.

TECHNICAL FIELD

Aspects of this invention relate generally to an apparatus for disposing dialysate and more particularly, to an apparatus with fittings to direct dialysate to a plumbing waste system in a safe, hygienic, and sanitary manner.

BACKGROUND

The dialysis process produces a waste discharge product known as dialysate effluent. The dialysate effluent includes human waste elements as well as reverse osmosis or other ultra-pure process water that is used in the dialysis process. Sanitizing solutions may also be pumped through the dialysis device so as to disinfect the dialysis device. This combination of discharged liquid wastes forming the dialysate effluent is generally corrosive and unsanitary (e.g., biohazardous) in nature and, therefore, may be hazardous to patients and medical staff, and to immunodeficient patients in particular.

When in hospitals, healthcare facilities, dialysis clinics, or other clinics that conduct dialysis services, this dialysis discharge typically flows through a dialysis box installed in a wall near the patient bed that is connected to the waste drain of a plumbing fixture. The dialysis box also has appropriate water supply connections in order to accommodate the fluid needs of the dialysis machine. This dialysate solution is highly concentrated, and without periodic rinse in the drain apparatus, damage can occur to the waste drain piping.

In other applications that do not have a dialysis box installed, the machine includes some alternative discharge for disposing the dialysate. Those other applications may be in an outpatient suite, or medical quick serve pharmacies, or at home. In these applications, patients often undergo dialysis in environments not primarily designed for this process, which has led to the practice of using fixtures, including toilets, lavatories, and shower stalls, to direct the dialysate effluent into a drain through discharge tubing coming from the output side of the dialysis unit. This is an unsanitary, non-hygienic practice that also produces risk to workers, residents, and patients that are exposed to the corrosive product that may spill or splash onto surfaces, or directly onto them. Since a dialysis procedure can last 3-4 hours or longer, there is a significant risk of exposure to the corrosive and unsanitary (e.g., biohazardous) discharged liquid.

Additionally, the unsanitary nature of the surfaces of a fixture and surfaces nearby can introduce germs, bacteria, and other contaminants to the discharge tubing of the dialysis device which can then be inadvertently transferred to workers and patients.

It would be desirable to provide a more hygienic, safe and convenient method of dialysate effluent disposal, and a dialysate disposal apparatus that reduces or overcomes some or all of the difficulties inherent in prior known processes. Particular objects and advantages will be apparent to those skilled in the art, that is, those who are knowledgeable or experienced in this field of technology, in view of the following disclosure and detailed description of certain embodiments.

BRIEF SUMMARY

General aspects of the present disclosure relate to a disposal system for dialysate effluent produced by a dialysis device during a dialysis process, which includes a fitting in fluid communication with the dialysis device and configured to discharge the dialysate effluent into the water flow path of a plumbing fixture to dispose of the dialysate.

Aspects of the disclosure relate to a dialysate disposal apparatus that includes a plumbing fixture having a water supply configured to supply water to the plumbing fixture and a drain configured to drain the water from the plumbing fixture, and a fitting configured for connection to the drain of the plumbing fixture. The fitting has an inlet port configured to receive dialysate effluent from a dialysis device, and the fitting is configured to discharge the dialysate effluent directly into the drain. For example, the fitting may be connected to piping within the drain or connected to the fixture at the drain opening to discharge the dialysate directly into the drain.

According to one aspect, the apparatus also includes a controller configured to control water flow through the water supply based on a characteristic of the dialysis process. The controller may be configured to activate or deactivate the water flow through the water supply based on the characteristic of the dialysis process.

According to another aspect, the plumbing fixture is a sink, and the fitting is connected to the drain at a location downstream from a trap of the drain. For example, the plumbing fixture may be a sink having a sink basin, and the drain includes a drain opening in the sink basin and a trap located downstream from the drain opening, where that the fitting is connected to the drain at a location downstream from the trap.

According to a further aspect, the plumbing fixture is a sink, and the fitting has an outlet extending into a drain opening of the drain to discharge the dialysate effluent directly into the drain. For example, the plumbing fixture may be a sink having a sink basin, and the drain includes a drain opening in the sink basin, where the fitting is connected to the sink at the drain opening and has an outlet extending into the drain opening to discharge the dialysate effluent directly into the drain.

According to yet another aspect, the inlet port is configured for connection to a conduit that is connected to the dialysis device.

Additional aspects of the disclosure relate to a dialysate disposal apparatus that includes a plumbing fixture having a water supply configured to supply water to the plumbing fixture, where the water supply includes water inlet piping, and a drain configured to drain the water from the plumbing fixture, and a fitting configured for connection to the water inlet piping of the plumbing fixture. The fitting has an inlet port configured to receive dialysate effluent from a dialysis device, and the fitting is configured to discharge the dialysate effluent directly into the water inlet piping.

According to one aspect, the apparatus also includes a controller configured to control water flow through the water supply based on a characteristic of the dialysis process. In one configuration, the controller is configured to activate or deactivate the water flow through the water supply based on the characteristic of the dialysis process.

According to another aspect, the plumbing fixture is a toilet, and the fitting is connected to the inlet piping at a location downstream from a flushometer of the water supply. For example, the plumbing fixture may be a toilet having a toilet basin, and the water supply includes a flushometer with the inlet piping connecting the flushometer to the toilet basin, where the fitting is connected to the inlet piping at a location downstream from the flushometer.

According to a further aspect, the inlet port is configured for connection to a conduit that is connected to the dialysis device.

Further aspects of the disclosure relate to a dialysate disposal apparatus that includes a dialysis device configured for a dialysis operation that produces a dialysate effluent, the dialysis device having a conduit through which the dialysate effluent is discharged from the dialysis device, a plumbing fixture having a water supply configured to supply water to the plumbing fixture and a drain configured to drain the water from the plumbing fixture, and a fitting configured for connection to the drain of the plumbing fixture. The fitting has an inlet port configured for connection to the conduit to receive the dialysate effluent from the dialysis device, and the fitting is configured to discharge the dialysate effluent into a water flow path of the plumbing fixture. The apparatus also includes a controller configured to control water flow through the water supply based on a characteristic of the dialysis process. The controller may be configured for receiving the characteristic of the dialysis process from an external computer device.

According to one aspect, the controller is configured to activate or deactivate the water flow through the water supply based on the characteristic of the dialysis process.

According to another aspect, the controller is configured to adjust a flow rate of the water flow through the water supply based on the characteristic of the dialysis process.

According to a further aspect, the plumbing fixture is a toilet and the water supply includes a flushometer, and the controller is configured for controlling the flushometer based on the characteristic of the dialysis process.

According to yet another aspect, the plumbing fixture is a sink and the water supply includes a faucet, and the controller is configured for controlling the faucet based on the characteristic of the dialysis process.

According to a still further aspect, the controller is further configured for controlling operation of the dialysis device. In one configuration, the controller is configured for controlling the water flow through the water supply by transmitting a signal to a second controller connected to the plumbing fixture and configured for directly controlling the water flow through the water supply. In another configuration, at least one of the fitting and the conduit has a sensor in communication with the controller, and the controller is configured to receive data transmitted by the sensor and to control operation of the dialysis device based on the data.

According to an additional aspect, the controller is configured to activate the water flow through the water supply based on the dialysis device completing the dialysis operation and all of the dialysate effluent being discharged into the plumbing fixture.

Other aspects of the disclosure relate to a fitting for a dialysate disposal apparatus that includes a fitting body configured for connection to water inlet piping of a plumbing fixture, an inlet port configured for connection to a conduit in communication with a dialysis device, such that the inlet port is configured to receive dialysate effluent through the conduit, and an outlet in fluid communication with the inlet port and configured for discharging the dialysate effluent received through the inlet port directly into the water inlet piping.

Other aspects of the disclosure relate to a fitting for a dialysate disposal apparatus that includes a fitting body configured for connection to drain piping of a plumbing fixture, an inlet port configured for connection to a conduit in communication with a dialysis device, such that the inlet port is configured to receive dialysate effluent through the conduit, and an outlet in fluid communication with the inlet port and configured for discharging the dialysate effluent received through the inlet port directly into the drain piping.

Other aspects of the disclosure relate to a fitting for a dialysate disposal apparatus that includes a fitting body configured for connection to a plumbing fixture having a drain with a drain opening, such that the fitting body is positioned at the drain opening and at least a portion of the fitting body is positioned outside the drain, an inlet port configured for connection to a conduit in communication with a dialysis device, such that the inlet port is configured to receive dialysate effluent through the conduit, and an outlet in fluid communication with the inlet port and configured for discharging the dialysate effluent received through the inlet port directly into the drain through the drain opening.

Other features and advantages of the disclosure will be apparent from the following description taken in conjunction with the attached drawings.

BRIEF DESCRIPTION OF THE DRAWINGS

The foregoing and other features and advantages of the present embodiments will be more fully understood from the following detailed description of illustrative embodiments taken in conjunction with the accompanying drawings in which.

The figures referred to above are not drawn necessarily to scale, should be understood to provide a representation of particular embodiments of the invention, and are merely conceptual in nature and illustrative of the principles involved. Some features of the dialysate disposal apparatus depicted in the drawings have been enlarged or distorted relative to others to facilitate explanation and understanding. The same reference numbers are used in the drawings for similar or identical components and features shown in various alternative embodiments. Dialysate disposal apparatuses as disclosed herein would have configurations and components determined, in part, by the intended application and environment in which they are used.

DETAILED DESCRIPTION OF EMBODIMENTS

Figure 1:
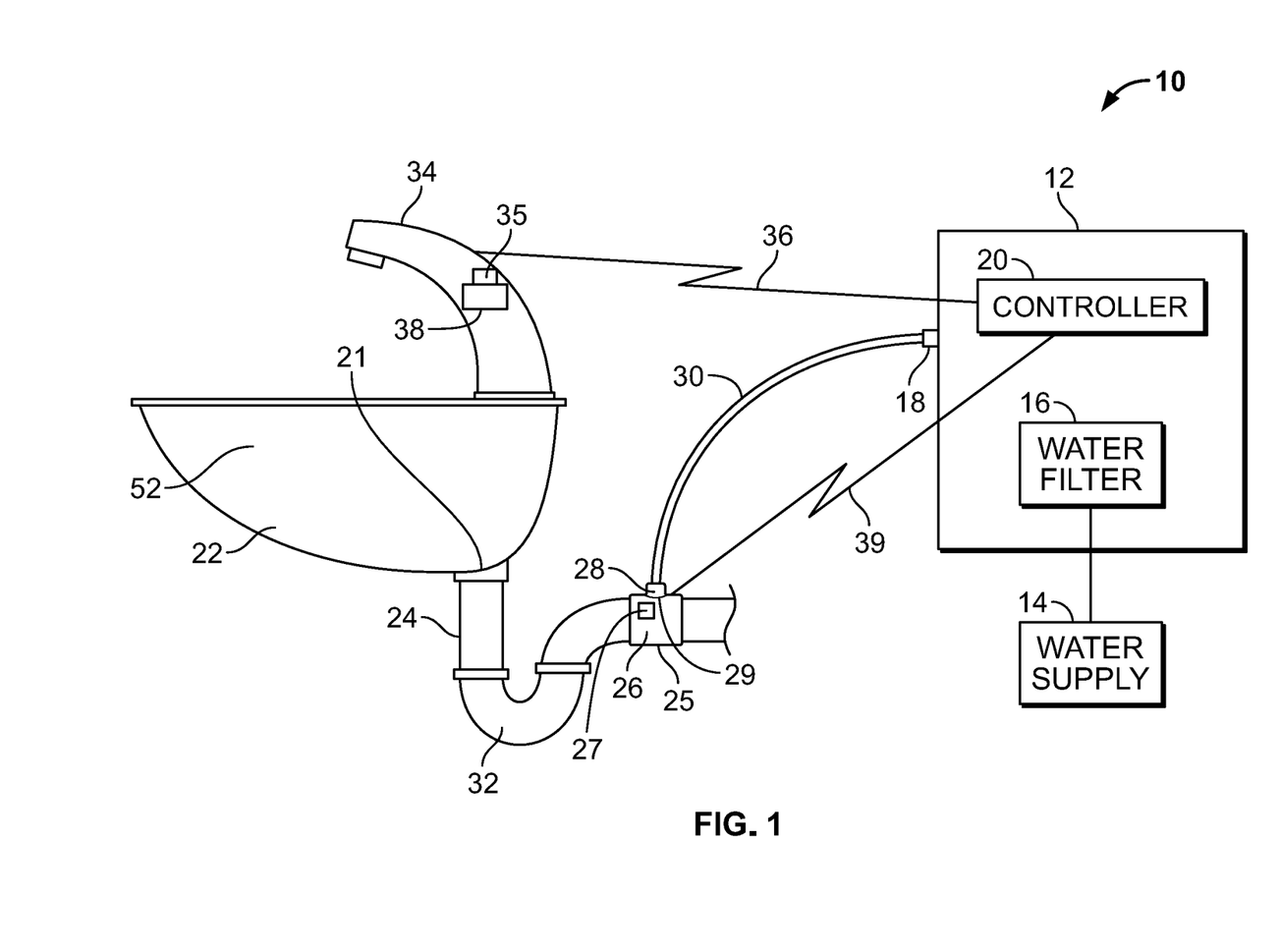
FIG. 1 is a schematic view of a plumbing fixture in the form of a sink and a dialysis device with a dialysate disposal apparatus connected thereto, according to aspects of the disclosure.
Figure 2:
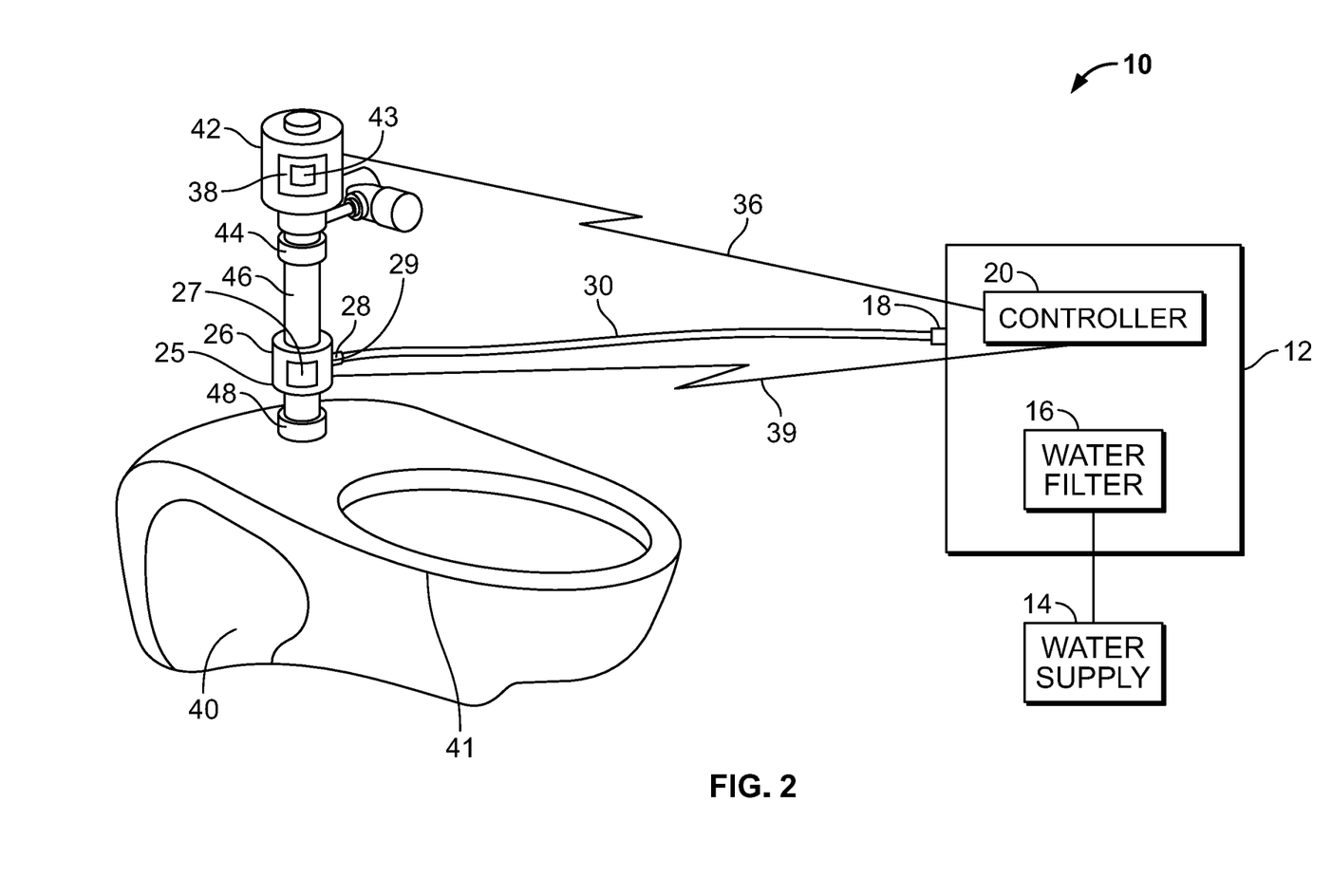
FIG. 2 is a schematic view of another embodiment of a plumbing fixture in the form of a toilet and a dialysis device with a dialysate disposal apparatus connected thereto according to aspects of the disclosure.
Figure 3:
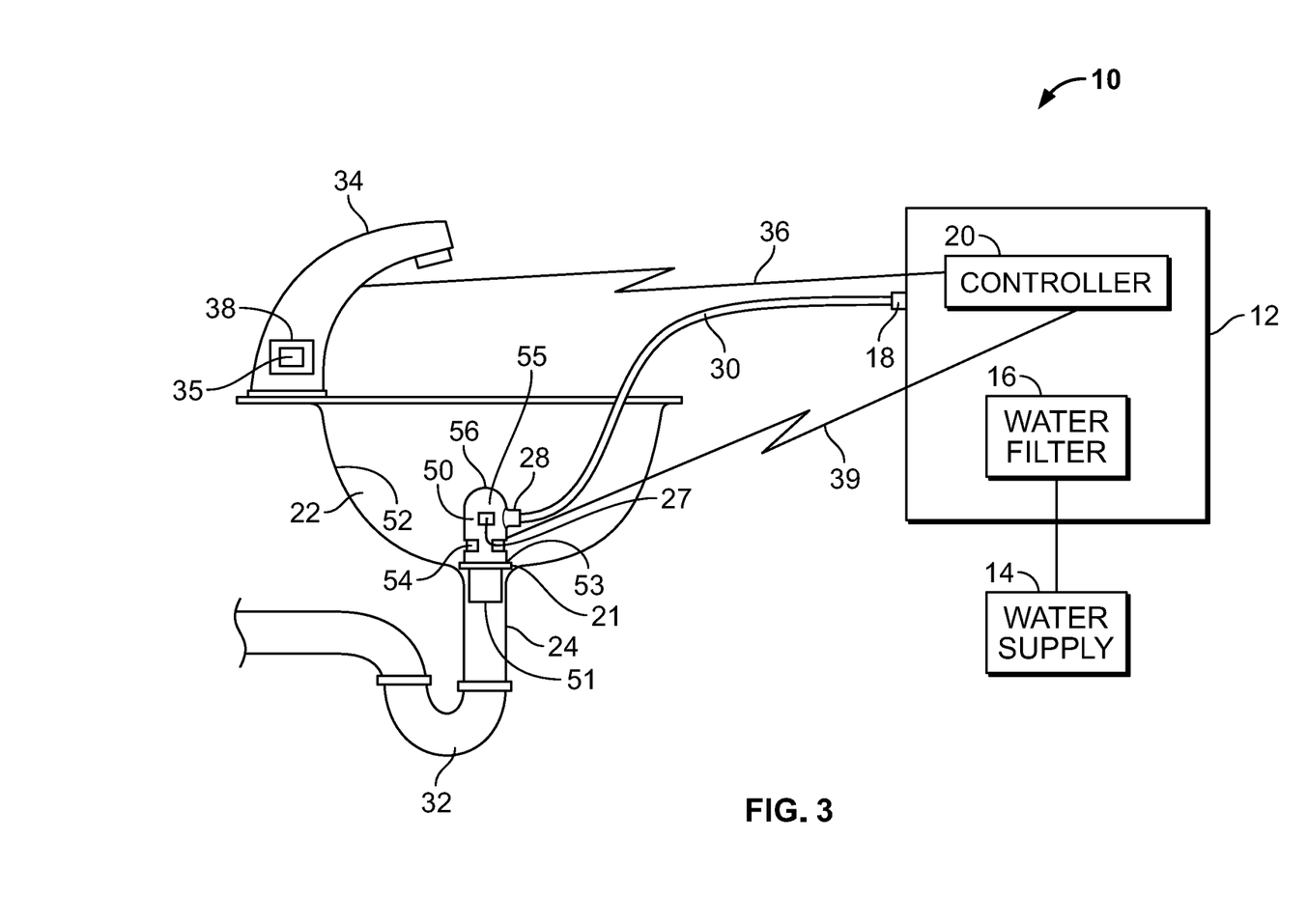
FIG. 3 is a schematic view of a further embodiment of a plumbing fixture in the form of a sink and a dialysis device with a dialysate disposal apparatus connected thereto according to aspects of the disclosure.

FIG. 1 illustrates a representative dialysate disposal apparatus 10. A dialysis device or machine 12, which is part of a dialysis treatment assembly, may be connected to a water supply 14 and may include a water filtering unit 16. The water filtering unit 16 may be a reverse osmosis filter that removes impurities and is used in the dialysis treatment. The dialysis device 12 may include an outlet port 18, where dialysate effluent is discharged from the dialysis device 12. The outlet port 18 is in communication with a component of the water flow path of a plumbing fixture, such as a sink 22 as shown in FIGS. 1 and 3 or a toilet 40 as shown in FIG. 2, and the apparatus 10 may include a conduit 30 connecting the outlet port 18 with the fixture 22, 40. The outlet port 18 and the conduit 30 are connected to the fixture 22, 40 such that the dialysate is discharged into the water flow path of the fixture 22, 40, such as within the water inlet piping or the drain of the fixture 22, 40. The apparatus 10 may discharge the dialysate through a fitting 26, 50 connected to the conduit 30 and configured to receive the dialysate from the dialysis device 12 and discharge the dialysate into the water flow path of the fixture 22, 40. In one embodiment, the fitting 26, 50 may be configured for connection to a drainage system or drain 24 of the fixture 22, 40, such that the fitting 26, 50 discharges the dialysate directly into the drain 24. In another embodiment, the fitting 26, 50 may be configured for connection to a water inlet system of the fixture 22, 40, such that the fitting 26, 50 discharges the dialysate directly into the inlet piping.

The dialysis device 12 may include a programmable controller 20 that serves to control operation of the dialysis device 12, including the flow of water from the water supply 14 to the water filtering unit 16. The controller 20 may be any type of programmable device suitable to control the dialysis device 12, and may include a processor, memory, and a communication interface. It is understood that the controller 20 and other controllers discussed herein may be embodied by multiple computer devices that are in communication with each other, and that such controllers may be configured to communicate over various different networks using various different wired and/or wireless communication techniques.

The controller 20 may further be programmed to control the flow of water into a plumbing fixture 22, 40 connected to a drain where the dialysate effluent is discharged. The sink 22 may include a drain 24, and a dialysate disposal fitting 26 may be connected to drain 24 to permit discharge of the dialysate effluent into the drain 24. The fitting 26 may include a fitting body 25 configured for connection to the drain 24 and an inlet port 28 connected to the fitting body 25 and connected to the outlet port 18 of the dialysis device 12 by the conduit 30. The fitting body 25 in FIG. 1 is connected to piping in the drain 24, and the outlet port 18 is removably connected to the conduit 30. The fitting 26 also has an outlet 29 in fluid communication with the inlet port 28 and the drain 24, such that the dialysate received through the inlet port 28 is discharged through the outlet 29 directly into the drain 24. It is to be appreciated that the conduit 30 may be flexible tubing, for example made out of appropriate material selected for the concentrated dialysate. The conduit 30 serves to carry the dialysate effluent from the dialysis device 12 to the drain 24 through the fitting 26.

In certain embodiments, the inlet port 28 may be or include a quick-connect fitting (with appropriate closing mechanics when disconnected) that allows the conduit 30 to be easily attached to, and removed from, the fitting 26. By providing a quick-connect fitting, a user can quickly and easily attach the conduit 30 to the fitting 26 in a hygienic manner, reducing the risk of contact with the corrosive dialysate effluent. The conduit 30 may additionally or alternately have a closing mechanism at one or both ends thereof, and may be configured for connection to a quick-connect fitting. The closing mechanisms on the inlet port 28 and/or the conduit 30 may be provided by a manually-activated, automatically-activated, or self-sealing valve, or another type of closing mechanism, in various embodiments. The use of the closing mechanism on the inlet port 28 and/or the conduit 30 prevents dialysate dripping while the conduit 30 is changed out. It is to be appreciated that the closing mechanism(s) on the inlet port 28 and/or the conduit 30 may be configured to be in a closed condition when the conduit 30 is not connected to the fitting 26, thereby preventing the leaking of any liquid out of the conduit 30 or the inlet port 28.

In embodiment of FIG. 1, the fitting 26 is connected to the drain 24 downstream of a basin 52 and the drain opening 21 of the sink 22, and also downstream of a trap 32 in the drain 24. It is to be appreciated that the fitting 26 could be connected to the drain 24 at different locations, such as between the drain opening 21 and the trap 32, and that any such connection will be in accordance with any relevant plumbing codes.

The plumbing fixture 22 may include a water supply assembly, such as a faucet 34. In one embodiment, when dialysate effluent is travelling from the dialysis device 12 into the drain 24, the faucet 34 may be turned on, causing water to flow into the drain 24. This water flow will dilute the dialysate effluent to reduce the corrosive nature of the effluent, and will also rinse or flush the dialysate effluent from surfaces (e.g., of the fixture 22 and/or the drain 24) that come into contact with the effluent to sanitize these surfaces. The faucet 34 may be turned on manually and/or automatically in various embodiments, as described herein.

In certain embodiments, the faucet 34 contains a controller 35 that can receive signals in order to control (e.g., change and/or activate) water flow at appropriate times and rates, in order to dilute and flush the effluent as described above. The controller 35 may include a processor, a memory, and communication interfaces, and may be in communication with another computer device from which the signals are received. In the embodiment of FIG. 1, the controller 35 is in communication with the controller 20 of the dialysis machine 12 and receives signals from the controller 20. A transmission medium 36 may connect the controller 20 of the dialysis machine 12 to the controller 35 of the electronic faucet 34, and carry a signal from controller 20 in order to control the flow of water from electronic faucet 34. The faucet 34 may be an electronic faucet where the controller 35 is also configured to control normal hand washing operations by detecting users and supplying water for standard hand washing practices, and the controller 35 may include a sensor for this purpose. The controller 35 may be programmed to control both the off and on function of electronic faucet 34, as well as regulate the flow (e.g., the flow rate) of water through electronic faucet 34, and the controller 35 may receive instructions from the controller 20 or another device to perform these actions.

In one embodiment, the flow of water through the faucet 34 can be optimized based on one or more characteristics of the dialysis process, e.g., characteristic(s) of the dialysate effluent being discharged into drain 24. The controller 20 may include logic for this optimization, such as for receiving one or more characteristics of the dialysis process and controlling the flow of water through the faucet 34 based on the characteristic(s). The controller 20 may further include logic for determining a desired adjustment to the water flow through the faucet 34 based on the characteristic(s), such that the controller 20 controls the flow of water through the faucet 34 based on the determination. The desired adjustment may be an activation or deactivation of the water flow and/or changing a flow rate of the water, among other adjustments.

The characteristic(s) of the dialysis process may be communicated to the controller 20 in various ways, such as by an external device storing data regarding such characteristics, sensors in communication with the controller 20 configured to gather data regarding such characteristics, and/or manual input. Examples of different characteristics that may be utilized by the controller 20 include properties of the dialysate effluent, flow status of the dialysate (e.g., whether the dialysate is flowing, about to flow, or just finished flowing, and/or a flow rate of the effluent), the source of the dialysate effluent, etc. One embodiment of optimization based on one such dialysis characteristic is providing full dilution and/or flushing of the dialysate effluent at known key times during the procedure, which may be determined by the controller 20 of the dialysate device 12 or received via input as described herein. Known key times may include times of highest dialysate flow rate, the end of the dialysis procedure, or a set periodic time throughout the procedure. For example, the controller 20 may be programmed to periodically flush water through the drain 24 after the conduit 30 has been disconnected, in order to ensure that no dialysate effluent remains in the drain 24 and/or to ensure that complete dilution and/or flushing is accomplished all the way downstream of the drain 24, the trap 32, the fitting 26, and other components. In another embodiment, the flow of water through the faucet 34 may be controlled based on the composition of the dialysate effluent. Other types of electronically automated fixtures 22, 40 (e.g., toilets) may be provided with a controller to control operation in a similar manner. The controller 20 and/or the controller 35 may further be configured to control operation of other electronically automated components associated with the fixture 22, 40, such as a hand dryer or soap dispenser (not shown). It is understood that a manually-activated faucet 34 may be provided with automated control features for automatic control of water flow through the faucet 34 and/or optimization of the same based on characteristics of the dialysis process as described above, in another embodiment.

It is to be appreciated that the transmission medium 36 may be a physical element, such as an electrical wire, cable, or optical fiber, for example. In other embodiments, transmission medium 36 may be a wireless link established by wireless signaling circuitry included in controller 20 and electronic faucet 34.

In certain embodiments, the fixture 22, 40 may include a user indicator 38, such as a display, audio component, LED, etc., which could provide visual and/or audible notice to the user related to operation of the fixture 22, 40. For example, the indicator 38 may indicate that the fixture 22, 40 is being controlled by another component (i.e., dialysis device 12 and/or controller 20). In this configuration, the indicator 38 may further indicate that the flow of water from faucet 34 is intentional and should not be interfered with and/or that the fixture 22, 40 is out of service for normal use, as well as potentially information (e.g., from controller 20) to approximate when the fixture 40 will again be available as normally. As another example, the user indicator 38 may indicate to the user that the fixture 22, 40 should be manually activated or deactivated (e.g., by turning on/off the faucet 34) to achieve proper dilution and flushing of the dialysate effluent. The user indicator 38 may include both visual and audio indications in one embodiment, for example, if a potential user of the fixture 22, 40 approaches for normal hand washing or other use and is not aware of the electronic display of the user indicator 38, an audio prompt may be generated from the user indicator 38 to draw attention to the display and/or inform the user of the status of the fixture 22, 40.

In certain embodiments, the fitting 26 and/or the conduit 30 may have a computer component 27 (e.g., with a processor, memory, and/or communications interfaces) connected to an external computer device via a communication medium 39 as described above, such as the controller 20 of the dialysis machine 12 as shown in FIGS. 1-3. The fitting 26 in FIG. 1 has a computer component 27 that includes a sensor, and this configuration could operate as a "smart" fitting 26 to communicate to the controller 20 and/or the water supply assembly (e.g., the controller 35), to provide an indication when the conduit 30 is connected to the inlet port 28 of the fitting 26. The fitting 26 and/or the conduit 30 may include one or more sensors 27 such as a connection sensor to detect connection of the conduit 30 to the inlet port 28 and/or a flow sensor to detect flow of dialysate through the conduit 30 or the inlet port 28. In such an embodiment, the controller 20 can be configured to control operation of the dialysis device 12 and/or the water supply based in part on data received from the sensor(s) 27, e.g., by commencing flow of dialysate effluent through the conduit 30 only when the controller 20 receives a signal from the sensor 27 to indicate that the conduit 30 is connected to the fitting 26. This would ensure that dialysate effluent is only carried through the conduit 30 when it is properly connected to the fitting 26. Thus, if a user were to place the end of the conduit 30 on the edge of the sink 22 or the toilet 40, no dialysate effluent would be allowed to flow into the sink 22 or the toilet 40. It is understood that such a sensor and/or computer device in communication with the controller 20 via communication medium 39 may be mounted on the conduit 30 as well. The conduit 30 and/or fitting 26 may likewise be provided with a sensor in communication with the controller 20 to indicate other conditions, such as whether or not fluid is flowing through the component and/or the flow rate of such fluid.

It is to be appreciated that portions of the fixture 22, 40 and the apparatus 10 may be formed of materials that are resistant to the corrosive effects of the dialysate effluent. For example, the conduit 30 and the fitting 26 may be formed of appropriate metallic alloys, plastics, ceramics, or combinations thereof.

Another embodiment of a dialysate disposal apparatus 10 is illustrated in FIG. 2, in which the plumbing fixture is a toilet 40. FIG. 2 depicts a wall mounted toilet, however the disposal apparatus 10 in FIG. 2 may be used with any floor mounted toilet configuration or other toilet configuration (e.g., a urinal). The water supply assembly of the toilet 40 may include a controller 43 that can receive signals in order to control water flow (e.g., by flushing the toilet 40) at appropriate times and rates, in order to dilute and flush the effluent as described above with respect to the controller 35 of the sink 22 in FIG. 1. The controller 43 may be configured to control an electronic flushometer 42 for automatically flushing the toilet 40 based on sensed user interaction in one embodiment, or a toilet 40 with a manual flushometer 42 or a separately-controlled electronic flushometer 42 may be outfitted with a controller 43 for receiving signals from an external device, e.g., the controller 20 of the dialysis machine 12. The controller 43 of the toilet 40 may include a processor, memory, a communication interface, and/or a sensor as similarly described with respect to the controller 35 of the sink 22, and the controller 43 may be similarly connected to the controller 20 by way of a communication medium 36. As discussed above, communication medium 36 may be a physical connection, such as a wire, cable, or optical fiber, or may be a wireless connection. The controller 43 may be configured for receiving signals from an external device (e.g., controller 20) to optimize flow of water through the toilet 40 based on one or more characteristics of the dialysis process being discharged into the toilet 40, as similarly described above with respect to the sink 22 in FIG. 1.

As illustrated in FIG. 2, the toilet 40 may include a vacuum breaker 44, and a dialysate disposal fitting 26 may be connected to the piping 46 of the toilet 40 downstream of both the flushometer 42 and the vacuum breaker 44, and upstream of a fixture spud 48 and the toilet basin 41 itself. The toilet 40 also has a drain (not shown) through which the contents of the toilet basin 41 and any water supplied through the piping 46 and the flushometer 42 are discharged from the toilet. In other embodiments, the fitting 26 may be connected to the toilet 40 at different locations. For example, the fitting 26 could be incorporated as part of the vacuum breaker 44 in one embodiment, or could be incorporated into the piping of the drain downstream of the toilet basin 41. It is to be appreciated that the connection of the fitting 26 to the toilet 40 will be in accordance with any relevant plumbing codes. The fitting 26 in the embodiment of FIG. 2 may be configured similarly to the fitting 26 described herein with respect to FIG. 1, such as including an inlet port 28 connected to the conduit 30, an outlet 29 in fluid communication with the inlet port 28 and the water inlet piping 46, such that the dialysate received through the inlet port 28 is discharged through the outlet 29 directly into the piping, a computer component 27 that includes a sensor, etc.

Portions of the toilet 40 may be formed of materials that are resistant to the corrosive effects of the dialysate effluent. For example, the fitting 26, the piping 44, the fixture spud 48, and the toilet basin 41 may be formed of engineered plastic, metallic alloys, ceramics, or suitable non-corroding combinations thereof.

The flushometer 42 can be a typical commercial grade plumbing fitting, capable of evacuating the toilet 40 with appropriate water supply after use with the toilet 42 as intended. The flushometer 42 can have a control which performs automatic operation according to pre-programmed inputs. For example, the flushometer 42 may be configured to activate flushing of the toilet 40 based on sensing of users at the toilet 40, and/or the flushometer 42 can have inputs configured to activate flushing of the toilet 40 according to known conditions of contents of the toilet 40 and/or the need to evacuate the basin 41. In one embodiment, the controller 20 can be configured to transmit signals (e.g., to the controller 43) to control and/or regulate the flow of water into the toilet 40 in order to provide full dilution and rinsing of the dialysate effluent being carried to the toilet 40 through the conduit 30, as well as to control the level of water in the basin 41 of the toilet 40 and/or the flow rate of water through the toilet 40, as similarly discussed above with respect to FIG. 1. Additionally, as similarly discussed above, the controller 20 of the dialysis device 12 may further transmit signals to control the operation of the flushometer 42, e.g., through the controller 43. The flushometer 42 can also allow for partial flushing depending upon the cycle of the dialysate device 12 of the existing cycle, such as by receiving signals from the controller 20. For example, the controller 20 may be configured to control the flushometer 42 to flush the toilet at selected times during the dialysate disposal procedure, such as discussed above with respect to the embodiment of FIG. 1.

In certain embodiments, the toilet 40 or the flushometer 42 thereof may include a user indicator 38, such as a display, an audio component, an LED, etc., which could provide a visual and/or audible notice that the toilet 40 is being controlled by another component (i.e., dialysis device 12 and/or controller 20), as similarly discussed above. Any of the indications discussed herein with respect to the user indicator 38 of FIG. 1 may be used in connection with the user indicator 38 of the toilet 40 in FIG. 2.

Another embodiment of a dialysate disposal apparatus 10 is illustrated in FIG. 3, in which a dialysate disposal fitting 50 is seated within a basin 52 of a sink 22. In such an embodiment, the fitting 50 includes a fitting body 55 seated over the drain 24 and directly in the drain 24, and the fitting 50 may be considered to be a drain fitting. At least a portion of the fitting body 55 may be positioned outside the drain 24 and within the basin 52 of the sink 22, and in the embodiment of FIG. 3, the fitting body 55 further has a portion that extends into and through the drain opening 21. A seal member, such as an O-ring 53, may be positioned about the fitting 50 in order to provide a seal between the fitting 50 and the opening 21 of the drain 24. The fitting 50 may also have mounting structure engaging the sink basin 52 and/or the drain 24 for securing the fitting 50 in place at or within the drain opening 21. The fitting 50 in this embodiment has an outlet 51 in fluid communication with the inlet port 28 and positioned within the drain opening 21 and extending into the drain 24, through which the dialysate effluent exits the fitting 50 into the drain 24. The outlet 51 of the fixture 50 in this configuration discharges the dialysate effluent at a location between the drain opening 21 and the drain trap 32. In another embodiment, the outlet 51 may be positioned and configured to discharge the dialysate effluent into the bottom of the basin 52, rather than directly into the drain 24. The conduit 30 is attached to the fitting 50 at an inlet port 28, and the conduit 30 and/or the inlet port 28 may include any components and features discussed above with respect to the conduit 30 and the inlet port 28 of the fitting 26 of FIGS. 1-2, such as quick-connect structures, shut-off valves, sensors, etc. Once this connection is made, the controller 20 may activate the flow of water from the faucet 34. The fitting 50 may be provided with one or more apertures 54 that allow water to flow from the basin 52 into the fitting 50 and the drain 24 and to dilute and rinse or flush away the dialysate effluent. In certain embodiments, a top surface 56 of the fitting 50 may be dome-shaped to reduce splashing when water falling from the faucet 34 strikes the fixture 50, in those instances where the faucet 34 outlet may be located directly above the fitting 50. In another embodiment, the top surface 56 of the fitting 50 may be open and funnel-shaped to allow and help guide water into the fixture 50, such that the water flows through the fixture 50 and into the drain 24.

As described above with respect to FIG. 1, the faucet 34 may include a controller 35 that can receive signals in order to control (e.g., change and/or activate) water flow at appropriate times and rates, in order to dilute and flush the effluent, and the controller 35 may do so in communication with and/or based on signals received from various sources, such as the controller 20 and/or sensors in communication with the controller 35. For example, as described above, the controller 20 can control electronic faucet 34 to discharge after dialysate operation is complete. In the embodiment of FIG. 3, this action is conducted so that the drain trap 32 can be completely evacuated of dialysate discharge and all remaining solutions are completely conveyed down the drain 24 for sanitary purposes, as well as to additionally dilute the effluent for complete transport from the dialysis operation. The corrosive nature of the dialysate effluent may deteriorate the fittings in the drain 24 if the dialysate effluent is not diluted and flushed from the drain trap 32 after completion of the dialysis process.

In another embodiment, the optimization of the water flow through the water inlet (e.g., the faucet 34 of flushometer 42) based on the characteristic(s) of the dialysis process may be performed by the controllers 35, 43 in conjunction with the controller 20 or independently of (and instead of) the controller 20. For example, the controller 35, 43 may receive information regarding the characteristic(s) o the dialysis process, determine a desired adjustment to the water flow based on the characteristic(s), and/or control the water flow based on the same. The controller 35, 43 may receive information from any of the sources discussed herein, including from the controller 20, in making these decisions. It is understood that any description herein of "a controller" performing an action or including logic to perform an action includes multiple controllers combining to perform the action or including logic to perform the action in combination with other controllers, unless the use of a single controller is explicitly specified.

Figure 4:
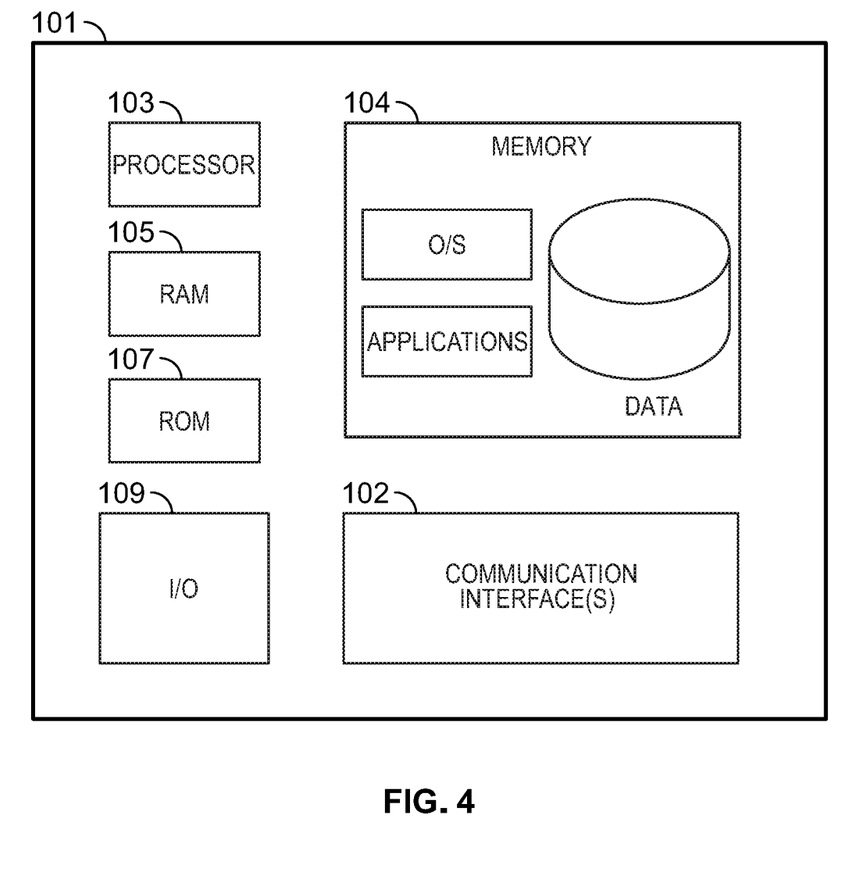
FIG. 4 is a schematic view of one embodiment of a computer device that is usable in connection with embodiments according to aspects of the disclosure.

FIG. 4 illustrates a block diagram of a computer device 101 that may be used according to an illustrative embodiment of the invention. The computer device 101 in FIG. 4 represents one embodiment of a structure for the various controllers 20, 35, 43, as well as any other computer component used with the apparatus 10, such as the computer component 27. The computer device 101 may have a processor 103 for controlling overall operation of the device 101 and its associated components, which may include components such as including RAM 105, ROM 107, an input/output module 109 for providing input to a user and/or receiving input from a user, and memory 104.

Software may be stored within memory 104 to provide instructions to processor 103 for enabling the computer device 101 to perform various functions, including functions relating to dialysate disposal and control of various plumbing fixtures. For example, memory 104 may store software used by the computer device 101, such as an operating system, application programs, and an associated database. Alternatively, some or all of computer device 101 computer executable instructions may be embodied in hardware or firmware (not shown).

The device 101 may be configured to operate in a networked environment supporting connections to one or more other computer devices and other devices (e.g., sensors) that communicate by wired or wireless communication media, via one or more communication interfaces 102. Such communications may be received and transmitted over a network such as a wide area network (WAN) or a local area network (LAN). The existence of any of various well-known protocols such as TCP/IP, FTP, HTTP and the like is presumed.

The various embodiments described herein provide benefits and advantages over existing dialysate disposal systems. For example, the dialysate disposal apparatus can be integrated into existing plumbing fixtures (e.g., sinks or toilets). As another example, the dialysate disposal apparatus can ensure that the dialysate effluent is discharged in a location where the risk of the effluent coming into contact with users of the fixture is minimized. As a further example, the dialysate disposal apparatus can be configured for controlling the flow of water through the fixture at desired times to dilute and flush the dialysate effluent from the fixture and the drain thereof, further minimizing potential risks such as corrosion of portions of the fixture and/or the dialysate effluent contacting a user of the fixture. Still other benefits and advantages are recognizable to those skilled in the art.

Various embodiments of dialysate disposal apparatuses have been described herein, which include various components and features. In other embodiments, the dialysate disposal apparatus may be provided with any combination of such components and features. It is also understood that in other embodiments, the various devices, components, and features of the dialysate disposal apparatus described herein may be constructed with similar structural and functional elements having different configurations, including different ornamental appearances.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Terms such as "top," "bottom," "front," "back," "side," and "rear," and the like, as used herein, are intended for illustrative purposes only and do not limit the embodiments in any way. Nothing in this specification should be construed as requiring a specific three-dimensional orientation of structures in order to fall within the scope of this invention, unless explicitly specified by the claims. Additionally, the term "plurality," as used herein, indicates any number greater than one, either disjunctively or conjunctively, as necessary, up to an infinite number. Accordingly, while the specific embodiments have been illustrated and described, numerous modifications come to mind without significantly departing from the spirit of the invention and the scope of protection is only limited by the scope of the accompanying claims.

What is claimed is:

1. A dialysate disposal apparatus comprising:
   a plumbing fixture having a water supply configured to supply water to the plumbing fixture and a drain configured to drain the water from the plumbing fixture;
   a fitting configured for connection to the drain of the plumbing fixture, the fitting having an inlet port configured to receive dialysate effluent from a dialysis device, wherein the fitting is configured to discharge the dialysate effluent directly into the drain; and
   a controller configured to control water flow through the water supply based on a characteristic of a dialysis process performed by the dialysis device.

2. The apparatus of claim 1, wherein the controller is configured to activate or deactivate the water flow through the water supply based on the characteristic of the dialysis process.

3. The apparatus of claim 1, wherein the inlet port has a connection fitting configured for releasable connection to a conduit in fluid communication with the dialysis device, and wherein the connection fitting comprises a quick-connect mechanism configured for connection to and disconnection from the conduit.

4. The apparatus of claim 1, wherein the inlet port has a connection fitting configured for releasable connection to a conduit in fluid communication with the dialysis device, and wherein the connection fitting comprises a closing mechanism configured for selectively permitting the dialysate effluent to flow through the inlet port.

5. The apparatus of claim 4, wherein the closing mechanism is configured to be automatically placed in a closed condition when the conduit is disconnected from the inlet port.

6. The apparatus of claim 1, wherein the plumbing fixture is a sink having a sink basin, and the drain comprises a drain opening in the sink basin and a trap located downstream from the drain opening, and the fitting is connected to the drain at a location downstream from the trap.

7. The apparatus of claim 1, wherein the plumbing fixture is a sink, and the fitting is connected to the drain at a location downstream from a trap of the drain.

8. The apparatus of claim 1, wherein the plumbing fixture is a sink having a sink basin, and the drain comprises a drain opening in the sink basin, and the fitting is connected to the sink at the drain opening and has an outlet extending into the drain opening to discharge the dialysate effluent directly into the drain.

9. The apparatus of claim 1, wherein the plumbing fixture is a sink, and the fitting has an outlet extending into a drain opening of the drain to discharge the dialysate effluent directly into the drain.

10. The apparatus of claim 1, wherein the inlet port is configured for connection to a conduit that is connected to the dialysis device.

11. The apparatus of claim 1, wherein the fitting is connected to piping within the drain.

12. A dialysate disposal apparatus comprising:
a dialysis device configured for a dialysis operation that produces a dialysate effluent, the dialysis device having a conduit through which the dialysate effluent is discharged from the dialysis device;
a plumbing fixture having a water supply configured to supply water to the plumbing fixture and a drain configured to drain the water from the plumbing fixture;
a fitting configured for connection to the drain of the plumbing fixture, the fitting having an inlet port configured for connection to the conduit to receive the dialysate effluent from the dialysis device, wherein the fitting is configured to discharge the dialysate effluent into a water flow path of the plumbing fixture; and
a controller configured to control water flow through the water supply based on a characteristic of the dialysis operation.

13. The apparatus of claim 12, wherein the controller is configured to activate or deactivate the water flow through the water supply based on the characteristic of the dialysis operation.

14. The apparatus of claim 12, wherein the controller is configured to adjust a flow rate of the water flow through the water supply based on the characteristic of the dialysis operation.

15. The apparatus of claim 12, wherein the plumbing fixture is a toilet and the water supply includes a flushometer, and wherein the controller is configured for controlling the flushometer based on the characteristic of the dialysis operation.

16. The apparatus of claim 12, wherein the plumbing fixture is a sink and the water supply includes a faucet, and wherein the controller is configured for controlling the faucet based on the characteristic of the dialysis operation.

17. The apparatus of claim 12, wherein the controller is further configured for controlling operation of the dialysis device.

18. The apparatus of claim 17, wherein the controller is configured for controlling the water flow through the water supply by transmitting a signal to a second controller connected to the plumbing fixture and configured for directly controlling the water flow through the water supply.

19. The apparatus of claim 17, wherein at least one of the fitting and the conduit has a sensor in communication with the controller, and wherein the controller is configured to receive data transmitted by the sensor and to control operation of the dialysis device based on the data.

20. The apparatus of claim 12, wherein the controller is configured to activate the water flow through the water supply based on the dialysis device completing the dialysis operation and all of the dialysate effluent being discharged into the plumbing fixture.

21. The apparatus of claim 12, wherein the controller is further configured for receiving the characteristic of the dialysis operation from an external computer device.

* * * * *